United States Patent
Lee et al.

(10) Patent No.: US 12,406,293 B2
(45) Date of Patent: Sep. 2, 2025

(54) SYSTEMS AND METHODS FOR GENERATING PERSONALIZED SKINCARE FORMULATIONS BASED ON BIOMARKER ANALYSIS

(71) Applicant: L'Oreal, Paris (FR)

(72) Inventors: Ji Lee, New York, NY (US); Guive Balooch, New York, NY (US); Fred Orsita, New York, NY (US); Edouard Messager, Paris (FR); Aude Foucher, Aulnay-sous-bois (FR); Nukhet Cavusoglu, Paris (FR)

(73) Assignee: L'Oreal, Paris (FR)

( * ) Notice: Subject to any disclaimer, the term of this patent is extended or adjusted under 35 U.S.C. 154(b) by 246 days.

(21) Appl. No.: 18/055,191

(22) Filed: Nov. 14, 2022

(65) Prior Publication Data
US 2023/0206300 A1    Jun. 29, 2023

Related U.S. Application Data

(63) Continuation of application No. 16/528,196, filed on Jul. 31, 2019, now Pat. No. 11,501,356.

(51) Int. Cl.
*G06Q 30/0601*   (2023.01)
*G01N 33/68*   (2006.01)
(Continued)

(52) U.S. Cl.
CPC ..... *G06Q 30/0631* (2013.01); *G01N 33/6881* (2013.01); *G05B 19/414* (2013.01);
(Continued)

(58) Field of Classification Search
CPC ..... G05B 2219/32287; G06Q 30/0621; G06Q 30/0631; G16B 50/00; G16H 20/10; G16H 50/20; G01N 33/6881
See application file for complete search history.

(56) References Cited

U.S. PATENT DOCUMENTS 10,025,280 B1    7/2018  Bly
11,501,356 B2 *  11/2022  Lee .................... G06Q 30/0621
(Continued)

FOREIGN PATENT DOCUMENTS

CN      105026930 A    11/2015
CN      106250670 A    12/2016
(Continued)

OTHER PUBLICATIONS

Office Action mailed May 23, 2023, in corresponding Japanese application No. 2022-506506, filed Nov. 4, 2019, 8 pages.
(Continued)

*Primary Examiner* — Vincent H Tran
(74) *Attorney, Agent, or Firm* — Christensen O'Connor Johnson Kindness PLLC

(57) ABSTRACT

Systems and methods are provided for improving skincare product formulations to address predicted skin trends. A biomarker analysis system is used to determine concentrations of various protein biomarkers of a user. A skin diagnosis computing device uses the protein biomarker concentrations to determine one or more skin trends, and determines one or more skincare product ingredients to address the skin trends. A skincare product is compounded that includes the one or more skincare product ingredients.

19 Claims, 4 Drawing Sheets

(51) Int. Cl.
  *G05B 19/414* (2006.01)
  *G16B 50/00* (2019.01)
(52) U.S. Cl.
  CPC ......... *G06Q 30/0621* (2013.01); *G16B 50/00* (2019.02); *G05B 2219/32287* (2013.01)

(56) References Cited

U.S. PATENT DOCUMENTS

| | | |
|---|---|---|
| 2005/0053637 A1 | 3/2005 | Ma'Or et al. |
| 2006/0265244 A1* | 11/2006 | Baumann ............... A61B 5/441 424/59 |
| 2008/0131902 A1 | 6/2008 | Maor et al. |
| 2009/0253162 A1 | 10/2009 | Windsor et al. |
| 2012/0184448 A1* | 7/2012 | Stella .................. A61K 8/03 506/7 |
| 2016/0016171 A1* | 1/2016 | Goel .................. C12N 15/1013 435/7.1 |
| 2016/0184566 A1 | 6/2016 | Ibrahim et al. |
| 2017/0322200 A1* | 11/2017 | Stella .................. G01N 33/5023 |
| 2017/0323057 A1* | 11/2017 | Karvela ............. G06Q 30/0631 |
| 2017/0340267 A1 | 11/2017 | Shen et al. |
| 2017/0343534 A1* | 11/2017 | Mills .................. G01N 33/5008 |
| 2018/0087097 A1* | 3/2018 | Toumazou .......... B01L 3/50273 |
| 2018/0131902 A1 | 5/2018 | Rosenberg |
| 2018/0260514 A1* | 9/2018 | Hosseini ................ G16B 20/00 |
| 2018/0284729 A1 | 10/2018 | Orsita et al. |
| 2018/0328945 A1* | 11/2018 | Nova .................. C12Q 1/6883 |
| 2018/0374567 A1* | 12/2018 | Toumazou ............. G16H 20/60 |
| 2019/0237194 A1 | 8/2019 | Salvi et al. |
| 2019/0292577 A1 | 9/2019 | Amini et al. |
| 2019/0295728 A1 | 9/2019 | Jeong et al. |
| 2019/0303991 A1 | 10/2019 | Ford |
| 2019/0369119 A1 | 12/2019 | Zhuang et al. |
| 2020/0102600 A1 | 4/2020 | Amini et al. |
| 2020/0154860 A1* | 5/2020 | Lee ........................ A45D 34/00 |
| 2020/0250866 A1 | 8/2020 | Balooch et al. |

FOREIGN PATENT DOCUMENTS

| | | |
|---|---|---|
| CN | 108289541 A | 7/2018 |
| CN | 108354587 A | 8/2018 |
| CN | 108701323 A | 10/2018 |
| JP | 2014041043 A | 3/2014 |
| JP | 2016538825 A | 12/2016 |
| JP | 2019102068 A | 6/2019 |
| KR | 20130135887 A | 12/2013 |
| KR | 20180080140 A | 7/2018 |
| WO | 2018/109078 A1 | 6/2018 |
| WO | 2018/115517 A1 | 6/2018 |
| WO | 2018/187151 A1 | 10/2018 |
| WO | 2019/038290 A1 | 2/2019 |
| WO | 2019/239120 A1 | 12/2019 |

OTHER PUBLICATIONS

Office Action mailed Oct. 5, 2022 issued in U.S. Appl. No. 16/528,380, filed Jul. 31, 2019, 11 pages.
International Search Report and Written Opinion mailed Jul. 30, 2021, issued in corresponding International Application No. PCT/US2020/042012, filed Jul. 14, 2020, 14 pages.
L'Oréal Brandstorm 2019—International Final Ceremony, YouTube clip, May 23, 2019, https://www.youtube.com/watch?v=CcLzr_4NhMA, Transcript 29 pages, see pp. 7-10 (timestamp 25:15 to timestamp 36:27).
"Presentation of Team PeauUnique at L'Oreal Brandstorm 2019, May 23, 2019, 10 pages."
Office Action mailed Oct. 30, 2024, in corresponding Japanese application No. 2024-060132, filed Jul. 14, 2020, 9 pages.
Office Action mailed Nov. 12, 2024, in corresponding Korean application No. 10-2022-7006298, filed Jul. 14, 2020, 14 pages.
Office Action mailed Mar. 5, 2025, in corresponding European application No. 20883687.4, filed Jul. 14, 2020, 8 pages.
Office Action mailed Jun. 19, 2025, in corresponding Chinese application No. 202080062859.9, filed Jul. 14, 2020, 19 pages.

* cited by examiner

SYSTEMS AND METHODS FOR GENERATING PERSONALIZED SKINCARE FORMULATIONS BASED ON BIOMARKER ANALYSIS

CROSS-REFERENCE TO RELATED APPLICATION

This application is a continuation of U.S. application Ser. No. 16/528,196, filed Jul. 31, 2019, now U.S. Pat. No. 11,501,356, issued Nov. 15, 2022, the entire disclosure of which is hereby incorporated by reference herein for all purposes.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a system for creating custom skincare products is provided. The system comprises a skincare product formulation device and a skin diagnosis computing device. The skin diagnosis computing device comprises at least one processor and a non-transitory computer-readable medium. The computer-readable medium has computer-executable instructions stored thereon that, in response to execution by the at least one processor, cause the skin diagnosis computing device to perform actions comprising: obtaining protein biomarker concentration information; determining at least one skincare product ingredient based on the protein biomarker concentration information; and transmitting the determined at least one skincare product ingredient to the skincare product formulation device. The skincare product formulation device is configured to receive the determined at least one skincare product ingredient; and dispense a skincare product that includes the at least one skincare product ingredient.

In some embodiments, a method for creating custom skincare products is provided. A skin diagnosis computing device obtains protein biomarker concentration information. The skin diagnosis computing device determines at least one skincare product ingredient based on the protein biomarker concentration information. The skin diagnosis computing device transmits the determined at least one skincare product ingredient to a skincare product formulation device for creation of a custom skincare product.

In some embodiments, a system for creating custom skincare products is provided. The system comprises circuitry for obtaining protein biomarker concentration information; circuitry for determining at least one skincare product ingredient based on the protein biomarker concentration information; and circuitry for transmitting the determined at least one skincare product ingredient to a skincare product formulation device for creation of a custom skincare product.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The medical field is currently being improved by the growing availability of biomarker analysis systems. These systems, which can operate in an outpatient or clinical setting, can provide a noninvasive measurement of various protein concentrations. These protein concentrations may then be used for various treatment-related purposes. Through clinical studies, certain proteins that can be detected by these biomarker analysis systems have been identified to be linked to clinical signs of aging, as well as responsiveness/non-responsiveness to various active ingredients of skincare products. For example, biomarkers such as YKL40, TG3, LCN1, IDE, and FLG2 have been found to be correlated with clinical signs of aging and responsiveness such as shiny skin, rough skin, uneven skin tone, eye wrinkles, photo aging, loss of elasticity, dilated pores, responsiveness to retinol, and responsiveness to proxylane.

Even though these correlations have been determined, the biomarker analysis system only provides raw protein concentration information, and does not use these correlations. What is desired are systems and methods that use the biomarker concentration information to improve skincare product formulations to address predicted skin trends.

Figure 1:
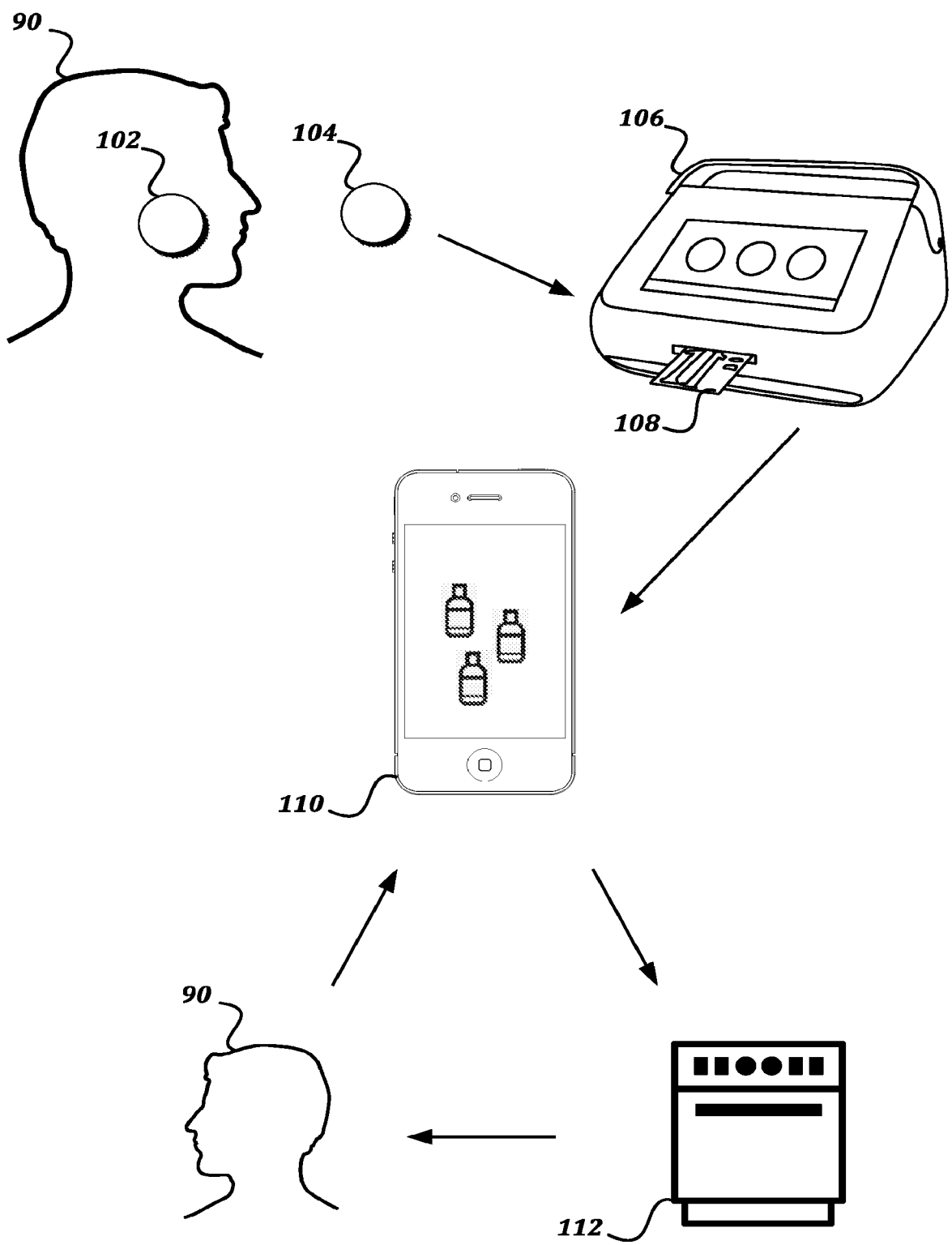
FIG. 1 is a high-level schematic drawing that illustrates various components of an example embodiment of a system according to various aspects of the present disclosure.

FIG. 1 is a high-level schematic drawing that illustrates various components of an example embodiment of a system according to various aspects of the present disclosure. The system is used to obtain a sample from a user 90, to generate skincare product formulations based on skin trends determined based on the sample, and to improve the skincare product formulations over time. As shown, one or more sampling disks 102, 104 are used to obtain a sample from the user 90. A sampling disk 104 is then processed by a protein extraction device 208, and a collected sample is applied to a test cartridge 108. The test cartridge 108 is inserted into an immunoassay analyzer device 106. The immunoassay analyzer device 106 determines concentrations of various protein biomarkers that are associated with various skin trends. The protein biomarker concentration information is then provided to a skin diagnosis computing device 110 to determine skin trends that are present. Based on the detected skin trends, a skincare product formulation device 112 may be used to create a custom skincare product to address the skin trends, and the user 90 may apply the custom skincare product. Feedback regarding the effectiveness of the custom skincare product may be provided back to the skin diagnosis computing device 110 or the skincare product formulation device 112 to improve future custom skincare products.

Figure 2:
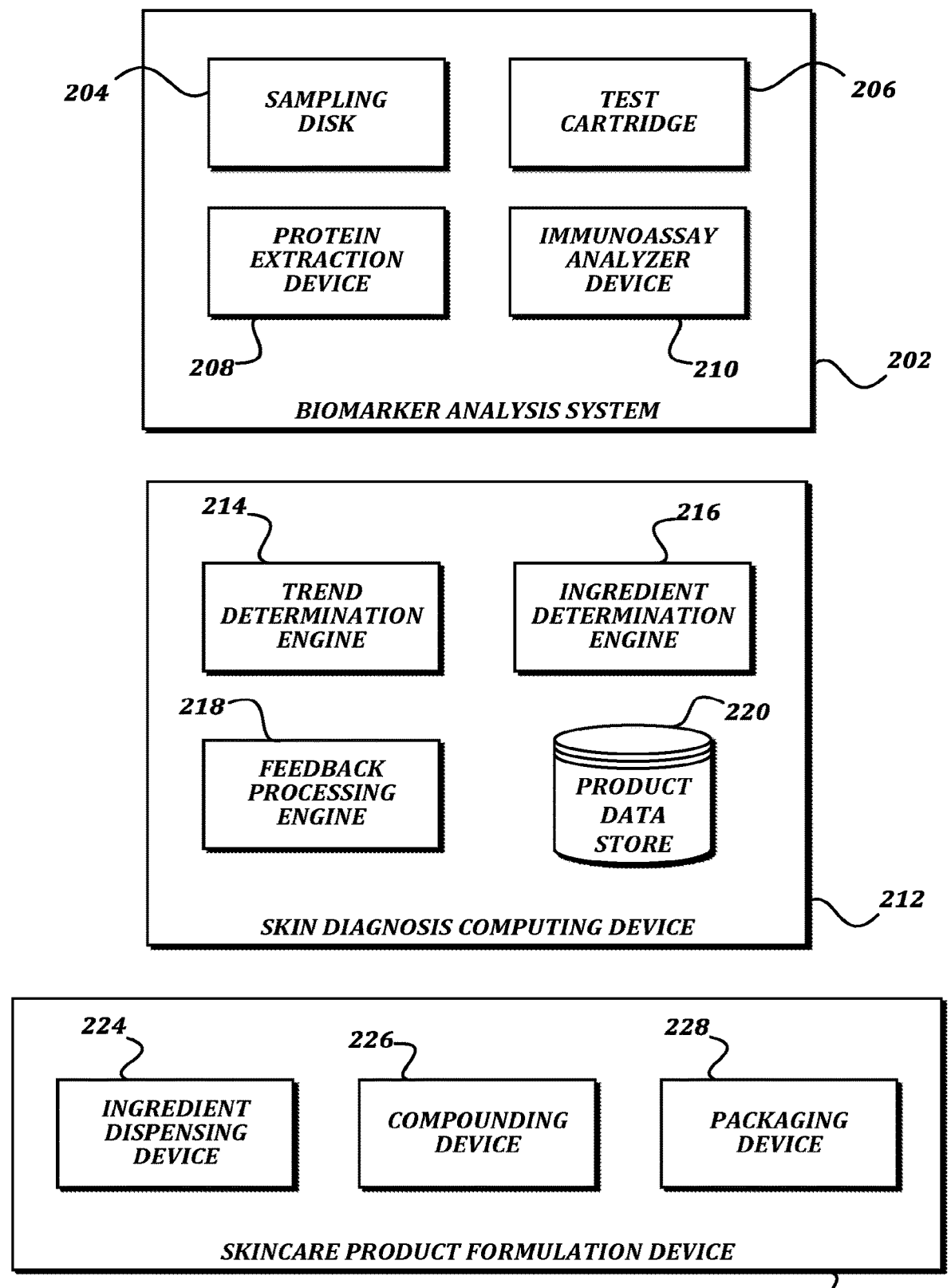
FIG. 2 is a block diagram that illustrates details of an example embodiment of a biomarker analysis system, a skin diagnosis computing device, and a skincare product formulation device according to various aspects of the present disclosure.

FIG. 2 is a block diagram that illustrates details of an example embodiment of a biomarker analysis system, a skin diagnosis computing device, and a skincare product formulation device according to various aspects of the present disclosure.

In some embodiments, the biomarker analysis system 202 includes one or more devices that provide a measurement of biomarkers sampled from a subject. In some embodiments, such sampling is done quickly and non-invasively, thus allowing the biomarker sampling to take place in an outpatient clinical or retail environment. In the illustrated embodiment, the biomarker analysis system 202 includes a sampling disk 204, a test cartridge 206, a protein extraction device 208, and an immunoassay analyzer device 210.

In some embodiments, the sampling disk 204 comprises a substrate and an adhesive. The adhesive is suitable for removably attaching the sampling disk 204 to the skin of a subject and obtaining a sample of skin cells therefrom. Though a sampling disk 204 is described, in some embodiments, an adhesive device of another shape, including but not limited to a rectangle or a tape may be used. In some embodiments, a swab, a wipe, or another device usable to collect a skin cell sample may be used instead of an adhesive device. One non-limiting example of a device that is suitable for use as a sampling disk 204 is a D-SQUAME® sampling disk produced by CuDerm Corporation, though other devices could be used.

In some embodiments, the protein extraction device 208 is configured to remove samples from sampling disks 204 and convert them into a form that can be provided to a test cartridge 206 for processing. In some embodiments, the protein extraction device 208 may include a container in which the sampling disk 204 may be placed along with a buffer solution. The protein extraction device 208 may also include a device for agitating, centrifuging, or otherwise processing the container such that the proteins from the collected skin sample are released from the sampling disk 204 and dissolved in the buffer solution.

In some embodiments, the test cartridge 206 is approximately the size of a credit card, and includes an inlet in which a droplet (approximately 30 µl) of the solution containing the proteins from the collected skin sample may be placed. The inlet may be coupled to one or more microfluidic channels through which the solution will automatically flow. In some embodiments, antibodies may be deposited within the one or more microfluidic channels, and antigens within the sample may react with the antibodies. This reaction may cause fluorescent beads associated with the antibodies to fluoresce according to the concentrations of the proteins being measured. The immunoassay analyzer device 210 may accept the test cartridge 206, and may measure the concentrations of the proteins of interest within the sample. In some embodiments, the immunoassay analyzer device 210 may do so by using laser light to determine which fluorescent beads are fluorescing. Once measured, the immunoassay analyzer device 210 may provide the determined protein concentrations to other components of the system using any suitable technique, including but not limited to presenting the protein concentrations on a display, printing the protein concentrations on a paper receipt, and electronically transmitting the determined protein concentrations to another device. One non-limiting example of an immunoassay analyzer device 210 (and its associated test cartridges 206) are the FREND™ System provided by NanoEnTek Inc.

In some embodiments, the skin diagnosis computing device 212 is a computing device configured to receive protein concentration information from the biomarker analysis system 202, determine one or more skin trends based on the protein concentration information, and determine recommended product ingredients based on the protein concentration information (and, in some embodiments, additional information gathered by the skin diagnosis computing device 212). The skin diagnosis computing device 212 may then provide the recommended product ingredients to a skincare product formulation device 222 in order to have a specialized product created, and may also receive feedback on the specialized product to improve future product ingredient recommendations.

In some embodiments, the skin diagnosis computing device 212 may be a mobile computing device such as a smartphone or a tablet computing device. In some embodiments, the skin diagnosis computing device 212 may be a desktop computing device or a laptop computing device. In some embodiments, the skin diagnosis computing device 212 may include more than one computing device, such as a user computing device configured to provide a user interface and one or more server computing devices configured to provide computational functionality (such as the functionality of the trend determination engine 214 and/or the ingredient determination engine 216 described below). In such embodiments, the user computing device and the one or more server computing devices may communicate via any suitable communication technology or technologies, such as a wired technology (including but not limited to Ethernet, USB, or the Internet) or a wireless technology (including but not limited to WiFi, WiMAX, 3G, 4G, LTE, or Bluetooth).

As shown, the skin diagnosis computing device 212 includes a trend determination engine 214, an ingredient determination engine 216, a feedback processing engine 218, and a product data store 220.

In some embodiments, the trend determination engine 214 is configured to receive protein biomarker concentration information from the biomarker analysis system, and to determine skin trends using the correlation information that has been clinically determined.

In some embodiments, the ingredient determination engine 216 is configured to receive the skin trend information and to determine one or more skincare product ingredients based on the skin trend information. In some embodiments, the ingredient determination engine 216 may directly use the protein biomarker concentration information to determine the skincare product ingredients. In some embodiments, the ingredient determination engine 216 may also collect additional information to inform the selection of skincare product ingredients, including but not limited to presenting a questionnaire that provides environmental information relevant to the user 90. In some embodiments, the ingredient determination engine 216 also provides the selected skincare product ingredients to the skincare product formulation device 222.

In some embodiments, the feedback processing engine 218 receives information from the user 90 regarding the effectiveness of the custom skincare products created from the instructions provided by the ingredient determination engine 216. The feedback processing engine 218 may store the information, and in some embodiments, the feedback processing engine 218 may cause the stored information to be used to improve selections of skincare product ingredients in the future.

In some embodiments, the product data store 220 may be used to store relevant information for each user 90, including but not limited to the protein biomarker concentration information, the additional information collected by the ingredient determination engine 216, the skin trends determined by the trend determination engine 214, the skincare product ingredients selected by the ingredient determination engine 216, and the feedback collected by the feedback processing engine 218.

In some embodiments, the skincare product formulation device 222 is configured to receive an indication generated by the skin diagnosis computing device 212 of ingredients that should be included in a custom skincare product. The skincare product formulation device 222 then generates and packages the custom skincare product. One non-limiting example of a skincare product formulation device 222 suitable for use in embodiments of the present disclosure is the Custom D.O.S.E, system provided by SkinCeuticals.

As shown, the skincare product formulation device 222 includes an ingredient dispensing device 224, a compounding device 226, and a packaging device 228. In some embodiments, the ingredient dispensing device 224 includes one or more components, such as pumps, droppers, pipettes, and spoons, that are capable of dispensing ingredients from ingredient storage associated with the skincare product formulation device. In some embodiments, the compounding device 226 is configured to receive the ingredients from the ingredient dispensing device 224 and to compound a final product by performing actions such as, but not limited to, grinding, agitating, and compacting. In some embodiments, the packaging device 228 may be configured to receive the compounded product from the compounding device 226 and place it in a container for delivery to the user 90. In some embodiments, the packaging device 228 may also be configured to seal and/or label the container.

Figure 3:
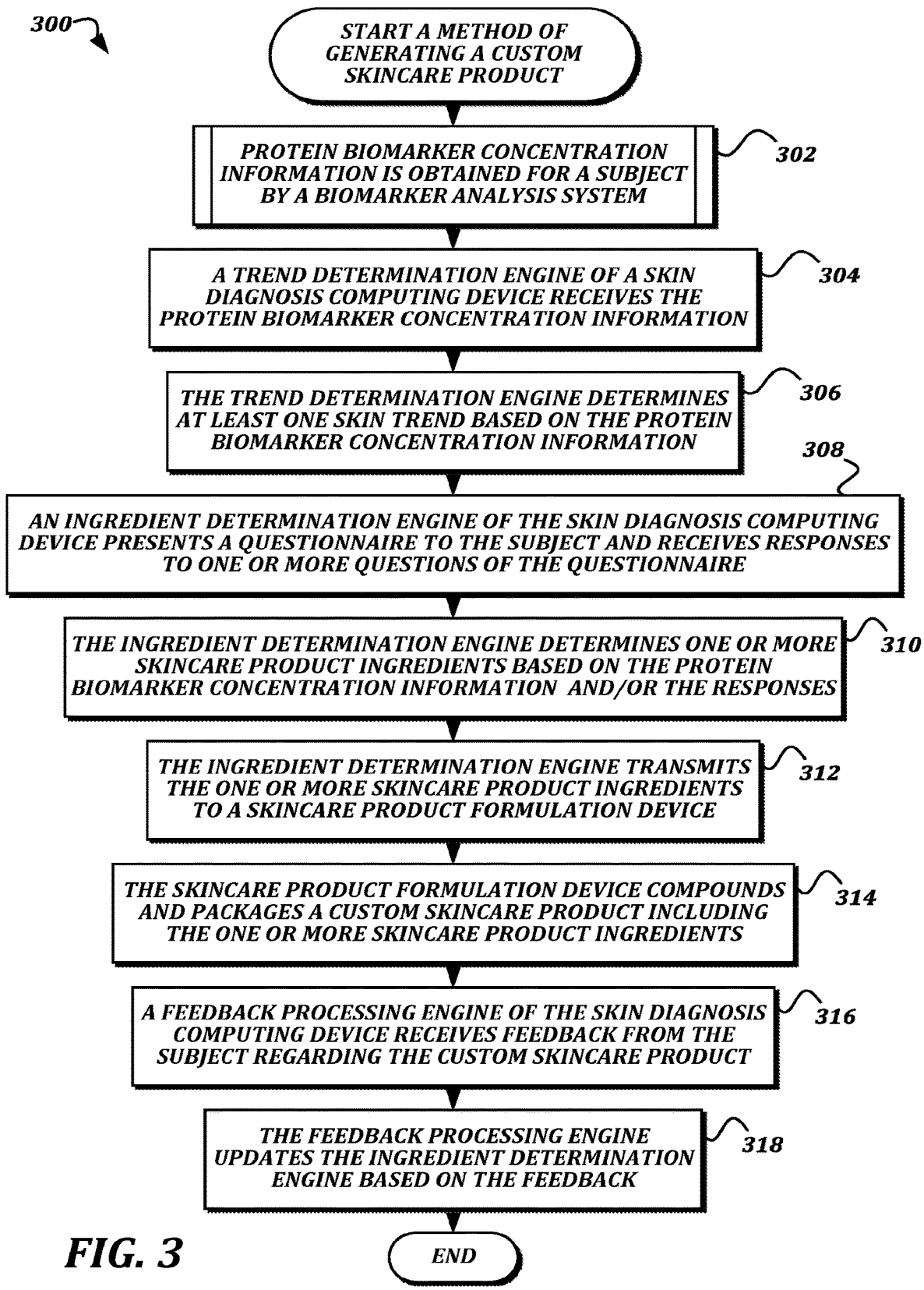
FIG. 3 is a flowchart that illustrates a method of generating a custom skincare product according to various aspects of the present disclosure.

FIG. 3 is a flowchart that illustrates a method of generating a custom skincare product according to various aspects of the present disclosure. From a start block, the method 300 advances to procedure block 302, where a procedure is executed wherein protein biomarker concentration information is obtained for a subject by a biomarker analysis system 202. Any suitable procedure may be used to collect the protein biomarker concentration information, including but not limited to the procedure 400 illustrated in FIG. 4 and described below.

At block 304, a trend determination engine 214 of a skin diagnosis computing device 212 receives the protein biomarker concentration information. In some embodiments, the protein biomarker concentration information is received from the biomarker analysis system 202 by the trend determination engine 214 via a network. The network may be a wireless network, including but not limited to a Wi-Fi network, a cellular network (including but not limited to a 3G network, a 4G network, a 5G network, or an LTE network), or a Bluetooth network; a wired network, including but not limited to an Ethernet network, a USB network, or a FireWire network; and/or any other type of network. In some embodiments, the protein biomarker concentration information may be displayed by a display device (not illustrated) of the biomarker analysis system 202, and the protein biomarker concentration information may be manually entered into an interface associated with the skin diagnosis computing device 212, or may be captured from the display device of the biomarker analysis system 202 by a camera of the skin diagnosis computing device 212.

At block 306, the trend determination engine 214 determines at least one skin trend based on the protein biomarker concentration information. Preliminary clinical studies have suggested linkage between five biomarkers (FLG2, TG3, IDE, LCN1, and YKL40) and clinical signs of aging. Example predictive performances (ROC curves) of these biomarkers for various clinical signs of aging are as follows:

| Clinical Sign | Biomarker | p value | Accuracy | Sensitivity | Specificity | kappa | Cutt off (ng/ml) |
|---|---|---|---|---|---|---|---|
| Shiny skin | FLG2 | 0.0000 | 66% | 77% | 53% | 0.30 | <166.3 |
| Rough skin | FLG2 | 0.0001 | 63% | 72% | 53% | 0.25 | <144.1 |
| Uneven skin tone | TG3 | 0.2048 | 60% | 67% | 46% | 0.12 | <26.8 |
| Eye wrinkles | IDE | 0.0000 | 62% | 67% | 58% | 0.24 | <11.5 |
| Photo-aging | TG3 | 0.0243 | 57% | 66% | 48% | 0.14 | <24.9 |
| Loss of Elasticity | LCN1 | 0.0201 | 57% | 57% | 56% | 0.13 | >44.3 |
| Dilated pores | YKL40 | 0.2245 | 54% | 61% | 51% | 0.10 | >2.4 |

Preliminary studies have also suggested a link between biomarkers and whether a subject is a responder or a non-responder to retinol and proxylane. Preliminary clinical studies have suggested that the YKL40 and TG3 biomarkers indicate that a subject will be responsive to retinol for improvement of underneath eye wrinkles, that the TG3 and LCN1 biomarkers indicate that a subject will be responsive to retinol for improvement of full-face dyschromia, and that the YKL40 biomarker indicates that a subject will be responsive to proxylane for improvement of crythrosis. In some embodiments, the trend determination engine 214 uses one or more of these clinically suggested relationships and the biomarker concentration information to predict one or more facial aging trends based on the biomarker concentration information. In some embodiments, the trend determination engine 214 may store the biomarker concentration information and/or the predicted facial aging trends/skin trends in the product data store 220.

The method 300 then proceeds to block 308, where an ingredient determination engine 216 of the skin diagnosis computing device 212 presents a questionnaire to the subject and receives responses to one or more questions of the questionnaire. The ingredient determination engine 216 may present the questionnaire to the subject using any suitable technique. In one non-limiting example, the ingredient determination engine 216 may present a user interface that includes the questions of the questionnaire on a display device (not illustrated) of the skin diagnosis computing device 212, and may receive answers via one or more human-machine interaction (HMI) devices (not illustrated) of the skin diagnosis computing device 212, including but not limited to a touch screen, a keyboard, a mouse, and a voice input system. In another non-limiting example, the ingredient determination engine 216 may present an audible question via a loudspeaker (not illustrated) of the skin diagnosis computing device 212, and may receive answers via a microphone and a voice recognition system (not illustrated). In yet another non-limiting example, the questionnaire may be presented on a sheet of paper or other physical embodiment, the subject may answer the questions on the sheet of paper, and the skin diagnosis computing device 212 may scan the answers from the sheet of paper using a camera (not illustrated), laser scanner, or other suitable device incorporated into or communicatively coupled to the skin diagnosis computing device 212. In some embodiments, the answers to the questions of the questionnaire are stored on a computer-readable medium accessible by the ingredient determination engine 216. In some embodiments, the questions of the questionnaire relate to environmental and/or behavioral factors that are likely to affect either facial aging trends or the effectiveness of a given product ingredient. Such environmental and/or behavioral factors include, but are not limited to, climate, humidity, stress level, sun exposure, diet, hydration, and smoking status.

At block 310, the ingredient determination engine 216 determines one or more skincare product ingredients based on the protein biomarker concentration information and/or the responses. As one non-limiting example, a particular skincare product ingredient may be associated with a particular skin trend to be addressed, and so the particular skincare product ingredient may be included by default if the skin trend is present based on the protein biomarker concentration information. As another non-limiting example, an optimal combination of skincare product ingredients may be included based on multiple skin trends if some of the skincare product ingredients can be used to address more than one skin trend. As yet another non-limiting example, a combination of ingredients that achieves optimum overall effectiveness in treating a combination of skin trends may be included if conflicting effects are present (e.g., if a first skincare product ingredient improves a first skin trend and a second skin trend but worsens a third skin trend, a second skincare product ingredient may be included to address the third skin trend, or a third skincare product ingredient may be included that addresses the first skin trend or the second skin trend instead of the first skincare product ingredient to avoid the worsening of the third skin trend). As still another non-limiting example, a skincare product ingredient may be chosen based on whether the protein biomarker concentration information indicates a responsiveness or a lack of responsiveness to the particular skincare product ingredient. In all of the above cases that describe selecting skincare product ingredients based on the skin trends or the protein biomarker concentration information, in some embodiments the selection may be made instead on the basis of the responses to the questionnaire, or on the basis of both the protein biomarker concentration information and the responses to the questionnaire.

At block 312, the ingredient determination engine 216 transmits the one or more skincare product ingredients to a skincare product formulation device 222. In some embodiments, the identities of ingredients, quantities of ingredients, relative concentrations of ingredients, type of medium for delivery, instructions for compounding, instructions for application, and/or other relevant information for the compounding and use of the custom skincare product may be transmitted by the ingredient determination engine 216. In some embodiments, the information is transmitted electronically using any wired or wireless technology described herein. In some embodiments, the ingredient determination engine 216 may cause the information to be presented on a display of the skin diagnosis computing device 212, and the information may be manually entered into an interface of the skincare product formulation device 222. In some embodiments, the ingredient determination engine 216 may cause the information to be printed on a hard copy of a form, and the form may be delivered to the skincare product formulation device 222 for entry. In some embodiments, the ingredient determination engine 216 may also store the information in the product data store 220.

At block 314, the skincare product formulation device 222 compounds and packages a custom skincare product including the one or more skincare product ingredients. In some embodiments, the skincare product formulation device 222 may combine one or more liquids, gels, powders, solutions, suspensions, serums, or other skincare product ingredients as specified by the information received from the ingredient determination engine 216. In some embodiments, the skincare product formulation device 222 may dispense the compounded custom skincare product into a container, may seal the container, and may label the container with one or more of an identification of the user 90, a list of ingredients in the custom skincare product, and a set of instructions for using the custom skincare product. The packaged custom skincare product is provided to the subject for use.

At block 316, a feedback processing engine 218 of the skin diagnosis computing device 212 receives feedback from the subject regarding the custom skincare product. In some embodiments, the subject provides feedback as responses to another questionnaire provided by a component of the skin diagnosis computing device 212, such as the feedback processing engine 218. In some embodiments, the questionnaire may include subjective feedback from the subject regarding their satisfaction with the custom skincare product. In some embodiments, the feedback may be objective feedback received from a skincare professional, or by re-testing the biomarkers using the biomarker analysis system 202. In some embodiments, the feedback may be input directly to the skin diagnosis computing device 212, while in other embodiments, the feedback may be collected by another device (such as the biomarker analysis system 202 or a computing device of the subject) and subsequently provided to the skin diagnosis computing device 212 using any suitable technique.

At block 318, the feedback processing engine 218 updates the ingredient determination engine 216 based on the feedback. In some embodiments, the ingredient determination engine 216 may use the feedback to update an effectiveness stored for each ingredient in the custom skincare product (e.g., increasing the stored effectiveness for skin trends that have improved with use, decreasing the stored effectiveness for skin trends that have not improved with use). In some embodiments, the ingredient determination engine 216 may use the feedback as training data for a machine learning system that is used to choose the ingredients based on the protein biomarker concentration information, the questionnaire responses, and/or the skin trends.

The method 300 then proceeds to an end block and terminates.

Figure 4:
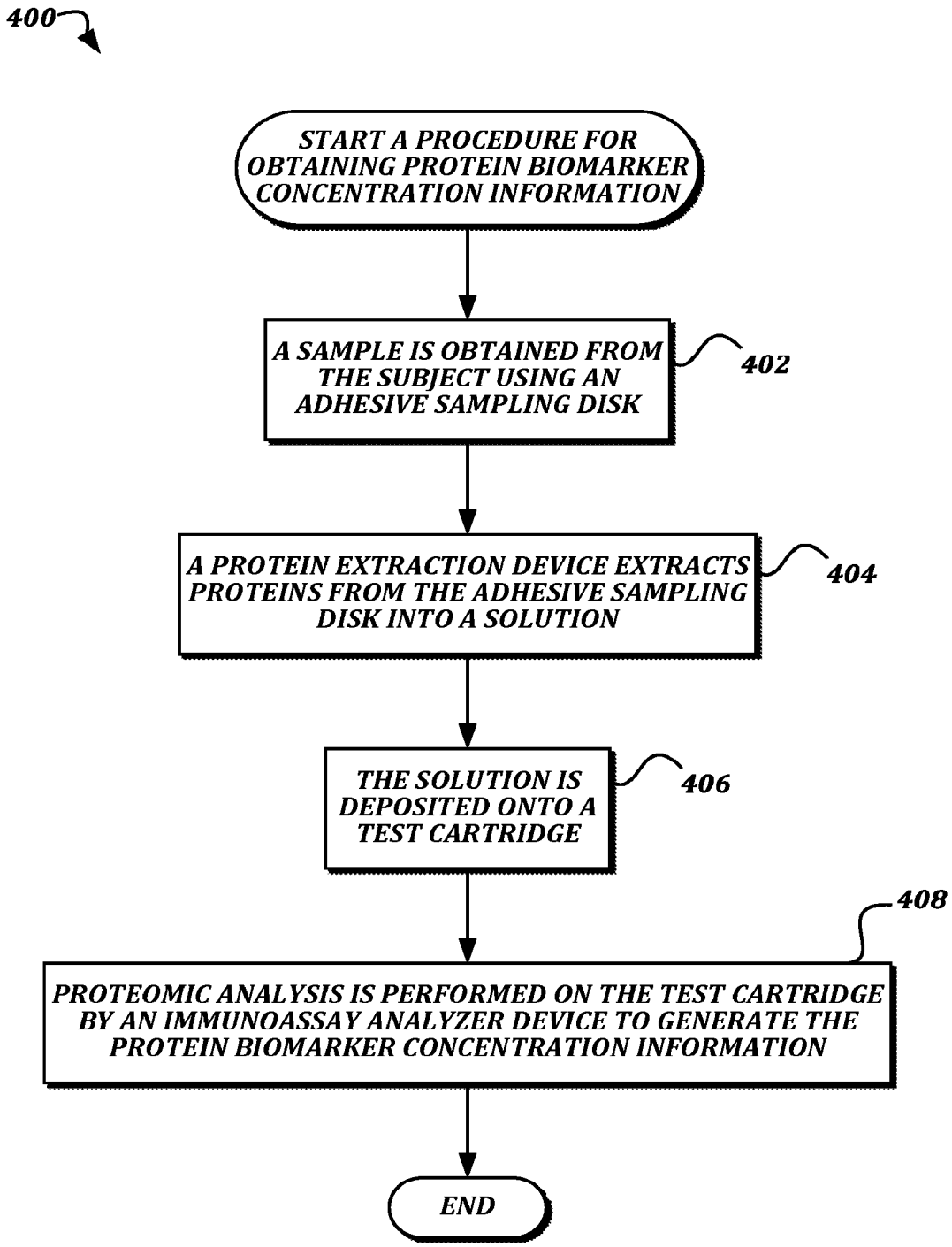
FIG. 4 is a flowchart that illustrates an example embodiment of a procedure for obtaining protein biomarker concentration information according to various aspects of the present disclosure.

FIG. 4 is a flowchart that illustrates an example embodiment of a procedure for obtaining protein biomarker concentration information according to various aspects of the present disclosure. The procedure 402 is a non-limiting example of a procedure suitable for use at block 302 of FIG. 3 for obtaining protein biomarker concentration information for a subject.

From a start block, the procedure 400 advances to block 402, where a sample is obtained from the subject using a sampling disk 204. In some embodiments, the sampling disk 204 may be attached to the skin of the subject via an adhesive. In some embodiments, the sampling disk 204 may absorb substances such as sweat, sebum, and other skin secretions. In some embodiments, the adhesive of the sampling disk 204 may collect skin cells from the skin of the subject. In some embodiments, the sampling disk 204 may be placed on the skin and removed from the skin multiple times to collect the skin sample. In some embodiments, a weight or pressure may be applied on top of the sampling disk 204, and/or the sampling disk 204 may be left in place for a specific amount of time, in order to obtain a consistent sample.

Next, at block 404, a protein extraction device 210 extracts proteins from the sampling disk into a solution. In some embodiments, the protein extraction device 210 may apply the solution to the sampling disk in order to dissolve the skin cells, skin secretions, or other sampled matter into the solution. In some embodiments, the sampling disk 204 may be placed in a buffer solution, and may then be shaken to cause the skin sample to be dissolved in the solution.

At block 406, the solution is deposited onto a test cartridge 206. In some embodiments, a droplet of the solution created by the protein extraction device 210 that includes the proteins from the sampling disk is placed in an inlet of the test cartridge 206.

At block 408, proteomic analysis is performed on the test cartridge 206 by an immunoassay analyzer device 208 to generate the protein biomarker concentration information. In some embodiments, the test cartridge 206 is inserted into the immunoassay analyzer device 208, which uses laser light to measure the fluorescing beads and thereby determine the concentrations of the protein biomarkers in the skin sample. The procedure 400 then advances to an end block and terminates. The protein biomarker concentration information may be displayed on a screen of the immunoassay analyzer device 208, may be transmitted electronically to another device, or may be provided to another device in some other way in order to allow the protein biomarker concentration information to be used for creating and updating skincare product formulations (or for any other purpose).

While illustrative embodiments have been illustrated and described, it will be appreciated that various changes can be made therein without departing from the spirit and scope of the invention.

The embodiments of the invention in which an exclusive property or privilege is claimed are defined as follows:

1. A non-transitory computer-readable medium having computer-executable instructions stored thereon that, in response to execution by one or more processors of one or more computing devices of a system, cause the system to perform actions for creating custom skincare products, the actions comprising:
   receiving, by a skin diagnosis computing device of the system, protein biomarker concentration information from an immunoassay analyzer device configured to determine protein concentrations from a sample provided by a subject by measuring fluorescence;
   determining, by the skin diagnosis computing device, at least one skincare product ingredient based on the protein biomarker concentration information; and
   transmitting, by the skin diagnosis computing device, the determined at least one skincare product ingredient to a skincare product formulation device of the system for creation of a custom skincare product.

2. The non-transitory computer-readable medium of claim 1, wherein the actions further comprise:
   receiving, by the skincare product formulation device, the determined at least one skincare product ingredient; and
   dispensing, by the skincare product formulation device, the custom skincare product that includes the at least one skincare product ingredient.

3. The non-transitory computer-readable medium of claim 1, wherein the actions further comprise:
   presenting, by the skin diagnosis computing device, a questionnaire; and
   receiving, by the skin diagnosis computing device, responses to questions of the questionnaire;
   wherein the determination of the at least one skincare product ingredient is further based on the responses.

4. The non-transitory computer-readable medium of claim 3, wherein the questionnaire includes questions directed to at least one of climate, humidity, stress level, and smoking status.

5. The non-transitory computer-readable medium of claim 1, wherein determining at least one skincare product ingredient includes using a recommendation engine that determines skincare product ingredients used by subjects with similar characteristics.

6. The non-transitory computer-readable medium of claim 5, wherein the actions further comprise:
   receiving, by the skin diagnosis computing device, feedback on skincare products from subjects; and
   updating, by the skin diagnosis computing device, the recommendation engine based on the feedback.

7. A skincare product formulation device, configured to perform actions comprising:
   receiving, from a skin diagnosis computing device, a determined at least one skincare product ingredient, wherein the at least one skincare product ingredient is determined by the skin diagnosis computing device by performing determination actions that include:
      receiving, protein biomarker concentration information from an immunoassay analyzer device configured to determine protein concentrations from a sample provided by a subject by measuring fluorescence; and
      determining the at least one skincare product ingredient based on the protein biomarker concentration information; and
   dispensing the custom skincare product that includes the at least one skincare product ingredient.

8. The skincare product formulation device of claim 7, further comprising an ingredient dispensing device, and wherein dispensing the custom skincare product that includes the at least one skincare product ingredient includes dispensing, by the ingredient dispensing device into a compounding device, the at least one skincare product ingredient from ingredient storage associated with the skincare product formulation device.

9. The skincare product formulation device of claim 8, wherein the actions further comprise compounding, by the compounding device, a final product by performing at least one of grinding, agitating, and compacting of the at least one skincare product ingredient.

10. The skincare product formulation device of claim 7, wherein the determination actions further include:
    presenting, by the skin diagnosis computing device, a questionnaire; and
    receiving, by the skin diagnosis computing device, responses to questions of the questionnaire;
    wherein the determination of the at least one skincare product ingredient is further based on the responses.

11. The skincare product formulation device of claim 10, wherein the questionnaire includes questions directed to at least one of climate, humidity, stress level, and smoking status.

12. The skincare product formulation device of claim 7, wherein determining at least one skincare product ingredient includes using a recommendation engine that determines skincare product ingredients used by subjects with similar characteristics.

13. The skincare product formulation device of claim 12, wherein the determining actions further include:
- receiving, by the skin diagnosis computing device, feedback on skincare products from subjects; and
- updating, by the skin diagnosis computing device, the recommendation engine based on the feedback.

14. A skin diagnosis computing device, comprising:
- at least one processor; and
- a non-transitory computer-readable medium having computer-executable instructions stored thereon that, in response to execution by the at least one processor, cause the skin diagnosis computing device to perform actions comprising:
  - receiving protein biomarker concentration information from an immunoassay analyzer device configured to determine protein concentrations from a sample provided by a subject by measuring fluorescence;
  - determining at least one skincare product ingredient based on the protein biomarker concentration information; and
  - transmitting the determined at least one skincare product ingredient to a skincare product formulation device.

15. The skin diagnosis computing device of claim 14, wherein the skin diagnosis computing device is a smartphone, a tablet computing device, a desktop computing device, or a laptop computing device.

16. The skin diagnosis computing device of claim 14, wherein the actions further comprise presenting a questionnaire and receiving responses to questions of the questionnaire; and wherein the determination of the at least one skincare product ingredient is further based on the responses.

17. The skin diagnosis computing device of claim 16, wherein the questionnaire includes questions directed to at least one of climate, humidity, stress level, and smoking status.

18. The skin diagnosis computing device of claim 14, wherein determining at least one skincare product ingredient includes using a recommendation engine that determines skincare product ingredients used by subjects with similar characteristics.

19. The skin diagnosis computing device of claim 18, wherein the actions further comprise:
- receiving feedback on skincare products from subjects; and
- updating the recommendation engine based on the feedback.

* * * * *